United States Patent
Han et al.

(10) Patent No.: US 10,557,781 B2
(45) Date of Patent: Feb. 11, 2020

(54) BENDING TEST DEVICE AND SYSTEM FOR FLEXIBLE DISPLAY DEVICE

(71) Applicant: WUHAN CHINA STAR OPTOELECTRONICS SEMICONDUCTOR DISPLAY TECHNOLOGY CO., LTD., Wuhan, Hubei (CN)

(72) Inventors: Wen Han, Hubei (CN); Rong Ma, Hubei (CN); Jichuan Liu, Hubei (CN)

(73) Assignee: WUHAN CHINA STAR OPTOELECTRONICS SEMICONDUCTOR DISPLAY TECHNOLOY CO., LTD., Wuhan, Hubei (CN)

( * ) Notice: Subject to any disclaimer, the term of this patent is extended or adjusted under 35 U.S.C. 154(b) by 140 days.

(21) Appl. No.: 15/735,311

(22) PCT Filed: Nov. 6, 2017

(86) PCT No.: PCT/CN2017/109518
§ 371 (c)(1),
(2) Date: Dec. 11, 2017

(87) PCT Pub. No.: WO2019/041546
PCT Pub. Date: Mar. 7, 2019

(65) Prior Publication Data
US 2019/0154555 A1    May 23, 2019

(30) Foreign Application Priority Data
Aug. 28, 2017   (CN) .......................... 2017 1 0748955

(51) Int. Cl.
*G01N 3/20*   (2006.01)
*G01N 3/04*   (2006.01)

(52) U.S. Cl.
CPC ............... *G01N 3/20* (2013.01); *G01N 3/04* (2013.01); *G01N 2203/0023* (2013.01); *G01N 2203/0282* (2013.01)

(58) Field of Classification Search
CPC .... G01F 1/1309; G01N 3/20; G01N 2203/0282; G01N 2203/0023; G01N 2203/0278
See application file for complete search history.

(56) References Cited

U.S. PATENT DOCUMENTS 3,831,438 A * 8/1974 Schmidt ................. G01N 3/32
                                                              73/852
4,179,941 A * 12/1979 Walter .................... G01N 3/20
                                                              73/854
(Continued)

FOREIGN PATENT DOCUMENTS

CN        200975965 Y     11/2007
CN        106596078 A      4/2017
(Continued)

OTHER PUBLICATIONS

English-language Machine Translation of CN-107014700-A which originally published on Aug. 4, 2017. (Year: 2017).*

*Primary Examiner* — David A Rogers
(74) *Attorney, Agent, or Firm* — Muncy, Geissler, Olds & Lowe, PC

(57) ABSTRACT

A bending test device and system for a flexible display device is provided. The bending test device has a bending device. The bending device has a bending shaft, an upper bending plate, and a lower fixing plate. An upper clamping plate is disposed on a surface of the upper bending plate. The upper clamping plate is configured to slide along the surface of the upper bending plate. A lower clamping plate is disposed on a surface of the lower fixing plate. The lower clamping plate is configured to slide along the surface of the lower fixing plate. A first tension measuring element con-
(Continued)

nects to an end of the upper clamping plate. A second tension measuring element connects to an end of the lower clamping plate.

10 Claims, 4 Drawing Sheets

(56) References Cited

U.S. PATENT DOCUMENTS

| | | | | |
|---|---|---|---|---|
| 5,574,227 A * | 11/1996 | Allan | ................... | G01N 3/20 73/849 |
| 6,053,052 A * | 4/2000 | Starostovic | ............. | G01N 3/20 73/851 |
| 7,516,644 B2 * | 4/2009 | Wong | ................... | G01N 3/20 73/12.06 |
| 7,591,189 B2 * | 9/2009 | MacKey | ............. | G01M 5/0033 73/852 |
| 7,882,748 B2 * | 2/2011 | Wen | ................... | G01N 3/20 73/760 |
| 7,971,492 B2 * | 7/2011 | Wen | ................... | G01N 3/20 73/849 |
| 8,461,860 B2 * | 6/2013 | Kim | ................... | G01M 5/005 324/762.01 |
| 8,806,953 B2 * | 8/2014 | Kim | ................... | G01N 3/20 310/49.01 |
| 8,943,898 B2 * | 2/2015 | Bell | ................... | G02F 1/133305 73/856 |
| 9,086,339 B2 * | 7/2015 | Lee | ................... | G01R 31/2893 |
| 9,354,150 B2 * | 5/2016 | Lee | ................... | G01N 3/20 |
| 9,940,859 B2 * | 4/2018 | Kim | ................... | G09G 3/006 |
| 10,054,527 B2 * | 8/2018 | Liu | ................... | G01M 99/007 |
| 10,094,752 B2 * | 10/2018 | Okazaki | ................... | G01N 3/20 |
| 10,197,482 B2 * | 2/2019 | Gao | ................... | G01N 3/00 |
| 2007/0193364 A1 * | 8/2007 | Wong | ................... | G01N 3/20 73/849 |
| 2007/0296452 A1 * | 12/2007 | Kang | ................... | G02F 1/133305 324/760.01 |
| 2008/0229844 A1 * | 9/2008 | Mackey | ............. | G01M 5/0033 73/852 |
| 2009/0272198 A1 * | 11/2009 | Wen | ................... | G01N 3/20 73/849 |
| 2011/0248739 A1 * | 10/2011 | Kim | ................... | G01M 5/005 324/762.01 |
| 2012/0067134 A1 * | 3/2012 | Bell | ................... | G02F 1/1309 73/800 |
| 2012/0285257 A1 * | 11/2012 | Kim | ................... | G01N 3/20 73/849 |
| 2014/0139252 A1 * | 5/2014 | Lee | ................... | G01R 31/2893 324/756.07 |
| 2014/0253160 A1 * | 9/2014 | Brunner | ................... | G09G 3/006 324/750.25 |
| 2014/0333333 A1 * | 11/2014 | Seol | ................... | G01R 31/2874 324/750.03 |
| 2015/0033870 A1 * | 2/2015 | Lee | ................... | G01N 3/20 73/849 |
| 2016/0086527 A1 * | 3/2016 | Kim | ................... | G09G 3/006 324/750.01 |
| 2016/0103048 A1 * | 4/2016 | Okazaki | ................... | G01N 3/20 73/853 |
| 2017/0102301 A1 * | 4/2017 | Liu | ................... | G01M 99/007 |
| 2017/0102302 A1 * | 4/2017 | Gao | ................... | G01N 3/00 |

FOREIGN PATENT DOCUMENTS

| | | | | | |
|---|---|---|---|---|---|
| CN | 106680108 A | * | 5/2017 | ............... | G01N 3/20 |
| CN | 106783660 A | * | 5/2017 | ............... | G01N 3/20 |
| CN | 106875849 A | | 6/2017 | | |
| CN | 106875849 A | * | 6/2017 | ............... | G02F 1/13 |
| CN | 107014700 A | | 8/2017 | | |
| CN | 206601304 U | * | 10/2017 | ............... | G01N 3/20 |
| CN | 108593471 A | * | 9/2018 | ............... | G01N 3/32 |
| CN | 108877608 A | * | 11/2018 | ............... | G01N 3/20 |
| CN | 208432497 U | * | 1/2019 | ............... | G01N 3/38 |
| CN | 109490117 A | * | 3/2019 | ............... | G01N 3/32 |
| JP | 201939743 A | * | 3/2019 | ............... | G01N 3/34 |
| KR | 20120010801 A | * | 2/2012 | | |
| KR | 20130111786 A | * | 10/2013 | | |
| KR | 101358732 B1 | * | 2/2014 | | |
| KR | 101489667 B1 | * | 2/2015 | | |
| KR | 101519561 B1 | * | 5/2015 | | |
| KR | 20160000925 A | * | 1/2016 | ............... | G01N 3/20 |
| KR | 20160000926 A | * | 1/2016 | ............... | G01N 3/20 |
| KR | 20160144694 A | * | 12/2016 | ............ | G01N 19/00 |
| KR | 20170048642 A | * | 5/2017 | ............... | G01N 3/38 |
| KR | 20180000130 A | * | 1/2018 | ............... | G01N 3/20 |
| KR | 20190010809 A | * | 1/2019 | ............... | G02F 1/13 |
| KR | 20190026207 A | * | 3/2019 | ............... | G01N 3/20 |
| WO | WO-2010138748 A2 | * | 12/2010 | ............ | G02F 1/1309 |
| WO | WO-2015064819 A1 | * | 5/2015 | ............... | G01N 3/20 |
| WO | WO-2018128265 A1 | * | 7/2018 | ............... | G01N 3/20 |
| WO | WO-2018155723 A1 | * | 8/2018 | ............... | G01N 3/34 |

* cited by examiner

BENDING TEST DEVICE AND SYSTEM FOR FLEXIBLE DISPLAY DEVICE

FIELD OF INVENTION

The present disclosure relates to a technical field of a flexible display device, and in particular to a bending test device and system for a flexible display device.

BACKGROUND OF INVENTION

With progress of science and technology, display technologies, such as liquid crystal displays (LCDs), plasma display panels (PDPs), and organic electroluminescence displays (OLEDs), are growing to maturity. Traditional displays, such as cathode ray tubes (CRTs) have already been replaced.

Recently, advantages of flexible display devices have become increasingly prominent. The flexible display devices refers to display devices in which a display panel is bendable and deformable. The flexible display devices have many types, such as flexible organic electroluminescent display devices, flexible electrophoresis display devices, or flexible liquid crystal display devices. A flexible display device includes at least one flexible display panel and a driving circuit controlling the flexible display panel, wherein the flexible display panel is made of a flexible material such that the flexible display panel is flexible, and the flexible display device is bendable.

A new generation of display devices have advantages such as being thin and light, having a high contrast, a fast response time, wide viewing angles, high brightness, and full color. Therefore, mobile phones, personal digital assistants (PDAs), digital cameras, car displays, laptops, wall-mounted TVs and the military are all very promising applications. In particular, the flexible display device can be kept in a bent state during storage for easy carrying. When working, it is easy to operate. It can also be hung on the body, showing a wearable state. There are many advantages to get more attention.

Flexible display devices and materials need to undergo a bending test to evaluate a bending radius of folding that the material and device can withstand, and the service life. Referring to FIGS. 1A to 1C, FIG. 1A is a schematic view of a flexible display device, wherein a display screen 10 of the flexible display device is disposed on a surface of the flexible display device. A flexible portion 11 is disposed on a side of the flexible display device. The flexible portion 11 can be made of rubber material. The flexible display device is bent inwardly. As shown FIG. 1B, the display screen 10 is located in a bending surface and can test the folding radius and the life of the inner fold. The flexible display device is bent outwards. As shown in FIG. 1C, the display screen 10 is located outside the bending surface and can test the folding radius and life of the outer fold.

However, there is no mechanism specially used for bending tests of a flexible display device in the prior art. As a result, an improved design of a bending test device and system for a flexible display device is provided, and solves the problems existing in conventional technologies.

SUMMARY OF INVENTION

An object of the present disclosure is to provide a bending test device and system for a flexible display device.

To achieve the above objects, the present disclosure provides a bending test device for a flexible display device, which comprises: a bending device comprises a bending shaft, an upper bending plate, and a lower fixing plate, wherein the bending shaft is disposed between the upper bending plate and the lower fixing plate, an end of the upper bending plate is fixedly connected to the bending shaft, the bending shaft is configured to rotate to move the upper bending plate to rotate toward the lower fixing plate, and the lower fixing plate is fixed on a workbench; an upper clamping plate disposed on a surface of the upper bending plate, wherein the upper clamping plate is configured to slide along the surface of the upper bending plate, a surface of the upper clamping plate that is away from the upper bending plate is an upper placing surface of the flexible display device, and the upper placing surface of the flexible display device is provided with a first fixing clip configured to fix an upper portion of the flexible display device; a lower clamping plate disposed on a surface of the lower fixing plate, wherein the lower clamping plate is configured to slide along the surface of the lower fixing plate, a surface of the lower clamping plate that is away from the lower fixing plate is a lower placing surface of the flexible display device, and the lower placing surface of the flexible display device is provided with a second fixing clip configured to fix a lower portion of the flexible display device; a first tension measuring element disposed on an upper portion of the upper bending plate and connected to an end of the upper clamping plate that is away from the bending shaft; a second tension measuring element disposed on a lower portion of the lower fixing plate and connected to an end of the lower clamping plate that is away from the bending shaft, and a flexible connection is at least formed between the first tension measuring element and the upper clamping plate, or formed between the second tension measuring element and the lower clamping plate; and a motion device connected to at least one end of the bending shaft and configured to drive the bending shaft to rotate, wherein the bending shaft and a connecting end of the motion device are provided with a gear, the motion device comprises a motor and a crank slider mechanism, the crank slider mechanism comprises a cam and a rack, the motor is connected to the cam through a driving shaft, the rack is connected to an edge of the cam through a connecting rod, the crank slider mechanism is configured to convert a rotational motion of the motor to a rectilinear motion of the rack, the rack is engaged with the gear of the bending shaft, and the rectilinear motion of the rack is converted to a rotational motion of the gear so that the bending shaft rotates.

To achieve the above objects, the present disclosure provides a bending test device for a flexible display device, which comprises: a bending device comprises a bending shaft, an upper bending plate, and a lower fixing plate, wherein the bending shaft is disposed between the upper bending plate and the lower fixing plate, an end of the upper bending plate is fixedly connected to the bending shaft, the bending shaft is configured to rotate to move the upper bending plate to rotate toward the lower fixing plate, and the lower fixing plate is fixed on a workbench; an upper clamping plate disposed on a surface of the upper bending plate, wherein the upper clamping plate is configured to slide along the surface of the upper bending plate, a surface of the upper clamping plate that is away from the upper bending plate is an upper placing surface of the flexible display device, and the upper placing surface of the flexible display device is provided with a first fixing clip configured to fix an upper portion of the flexible display device; a lower clamping plate disposed on a surface of the lower fixing plate, wherein the lower clamping plate is configured to slide along the surface of the lower fixing plate, a surface of the lower clamping plate that is away from the lower fixing plate is a lower placing surface of the flexible display device, and the lower placing surface of the flexible display device is provided with a second fixing clip configured to fix a lower portion of the flexible display device; a first tension measuring element disposed on an upper portion of the upper bending plate and connected to an end of the upper clamping plate that is away from the bending shaft; and a second tension measuring element disposed on a lower portion of the lower fixing plate and connected to an end of the lower clamping plate that is away from the bending shaft.

In one embodiment of the present disclosure, the bending test device further comprises a motion device, the motion device is connected to at least one end of the bending shaft and configured to drive the bending shaft to rotate.

In one embodiment of the present disclosure, the bending shaft and a connecting end of the motion device are provided with a gear, the motion device comprises a motor and a crank slider mechanism, the crank slider mechanism comprises a cam and a rack, the motor is connected to the cam through a driving shaft, the rack connects to an edge of the cam through a connecting rod, the crank slider mechanism is configured to convert a rotational motion of the motor to a rectilinear motion of the rack, the rack is engaged with to the gear of the bending shaft, and the rectilinear motion of the rack is converted to a rotational motion of the gear so that the bending shaft rotates.

In one embodiment of the present disclosure, the motor is connected to the driving shaft through a transmission belt.

In one embodiment of the present disclosure, a shaft sleeve is disposed on the bending shaft, at least one bearing is disposed in the shaft sleeve so that the shaft sleeve and the flexible display device have synchronized movement.

In one embodiment of the present disclosure, the bending test device further comprises an angle plate. The angle plate is disposed on the bending shaft and located at a side of the upper bending plate, the angle plate is formed with an angular scale.

In one embodiment of the present disclosure, a flexible connection is at least formed between the first tension measuring element and the upper clamping plate, or formed between the second tension measuring element and the lower clamping plate.

In one embodiment of the present disclosure, a surface of upper bending plate is disposed with a first slide, and the upper clamping plate is disposed with a first chute corresponding to the first slide, the first chute slides along the first slide so that the upper clamping plate slides along the surface of the upper bending plate; a surface of lower fixing plate is disposed with a second slide, and the lower clamping plate is disposed with a second chute corresponding to the second slide, the second chute slides along the second slide so that the lower clamping plate slides along the surface of the lower fixing plate.

In one embodiment of the present disclosure, a bending test system for a flexible display device includes a plurality of bending test devices for a flexible display device.

In one embodiment of the present disclosure, each of two adjacent bending test devices are driven through a transmission belt disposed on a driving shaft, a motor connects to one of the bending test devices so that all bending test devices are driven by the transmission belt.

The beneficial effect of the present disclosure is that a bending test device for a flexible display device is provided, wherein the structure is simple, and the operation method is easy. It can measure the bending stress of the flexible display device at different bending angles, and evaluate the bending ability of the flexible display device.

DETAILED DESCRIPTION OF PREFERRED EMBODIMENTS

The specific embodiments of a bending test device and system for a flexible display device provided by the present disclosure are described in detail below with reference to the accompanying drawings.

Figure 1A:
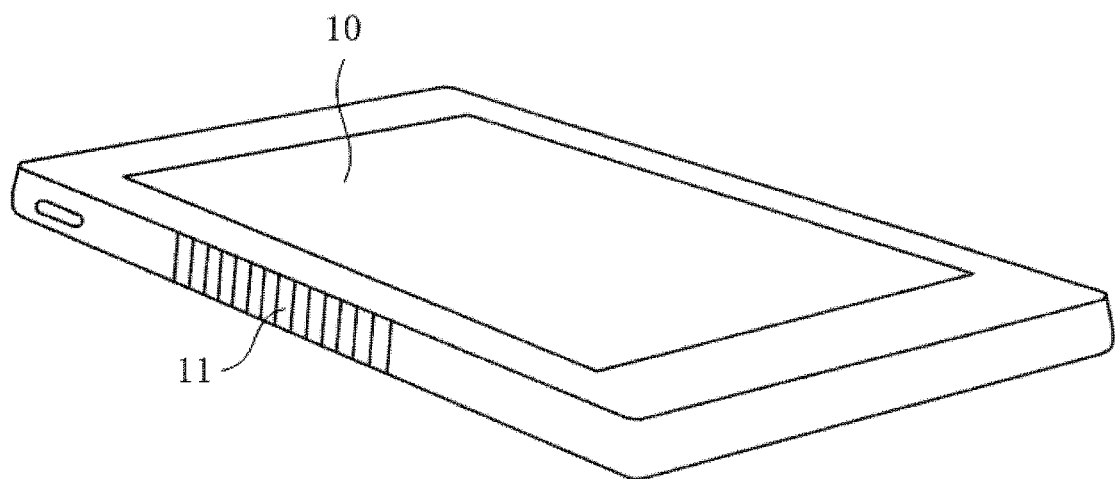
FIG. 1A is a schematic view of a flexible display device.
Figure 1B:
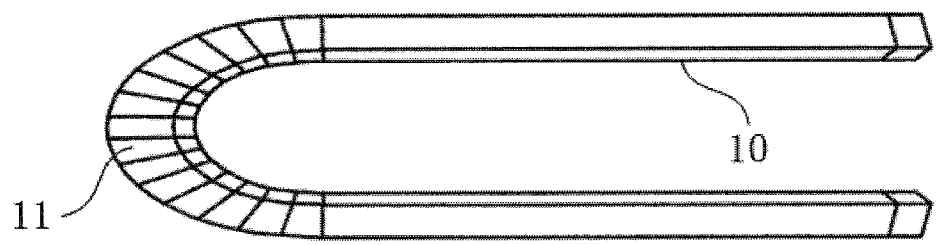
FIG. 1B is a schematic view of the flexible display device bent inward.
Figure 1C:
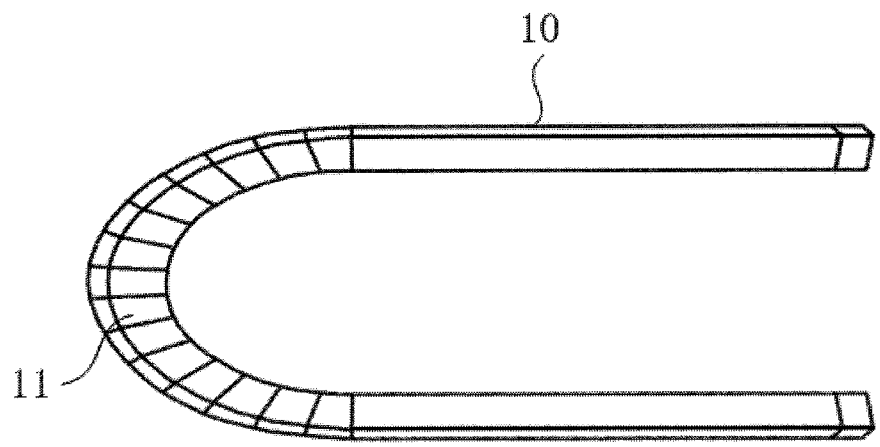
FIG. 1C is a schematic view of the flexible display device bent outward.
Figure 2:
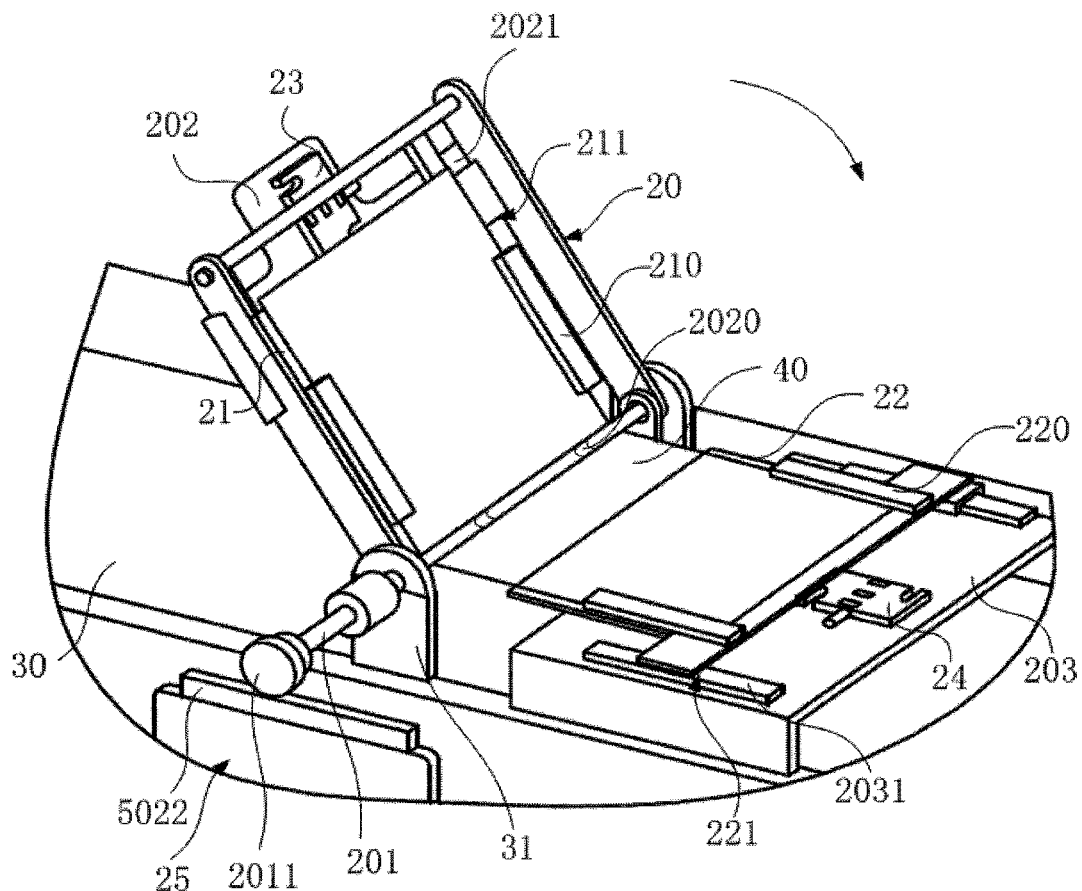
FIG. 2 is a schematic view of a bending test device for the flexible display device of the present disclosure.

Referring to FIG. 2, a schematic view of a bending test device for a flexible display device of the present disclosure is illustrated. The bending test device for the flexible display device comprises a bending device 20, an upper clamping plate 21, a lower clamping plate 22, a first tension measuring element 23, and a second tension measuring element 24.

The bending device 20 comprises a bending shaft 201, an upper bending plate 202, and a lower fixing plate 203. The bending shaft 201 is disposed between the upper bending plate 202 and the lower fixing plate 203. The bending shaft 201 is supported through a stand 31 fixed on a workbench 30. An end of the upper bending plate 202 is fixedly connected to the bending shaft 201, wherein the fixed connection is a removable fixed connection. The bending shaft 201 is configured to rotate to move the upper bending plate 202 to rotate toward the lower fixing plate 203. The movement direction of the upper bending plate 202 is shown as an arrow in FIG. 2. The bending shaft 201 can rotate by driving a motion device 25, the specific structure of the motion device 25 will be described below. The bending shaft 201 and the lower fixing plate 203 are not touched to avoid the lower fixing plate 203 being rotated by driving the bending shaft 201. The lower fixing plate 203 is fixed on the workbench 30, and the lower fixing plate 203 is not rotated and slid.

A surface of upper bending plate 202 is disposed with a first slide 2021, wherein the first slide 2021 comprises two tracks disposed on the upper bending plate 202. A surface of lower fixing plate 203 is disposed with a second slide 2031, wherein the second slide 2031 comprises two tracks disposed on the lower fixing plate 203.

The upper clamping plate 21 is disposed on the surface of upper bending plate 202, and the upper clamping plate 21 is disposed with a first chute 211 corresponding to the first slide 2021, the first chute 211 slides along the first slide 2021 so that the upper clamping plate 21 slides along the surface of the upper bending plate 202. A surface of the upper clamping plate 21 that is away from the upper bending plate 202 is an upper placing surface of the flexible display device. Furthermore, the first chute 211 is disposed on the surface of the upper clamping plate 21 facing the upper bending plate 202. The upper placing surface of the flexible display device is provided with a first fixing clip 210, and the first fixing clip 210 is disposed on two sides of the upper clamping plate 21. The first fixing clip 210 is configured to fix an upper portion of the flexible display device so that the flexible display device is fixed on the upper clamping plate 21. When the upper clamping plate 21 is slid relative to the surface of the upper bending plate 202, the flexible display device is stopped relative to the upper clamping plate 21.

The lower clamping plate 22 is disposed on a surface of the lower fixing plate 203. The lower clamping plate 22 is disposed with a second chute 221 corresponding to the second slide 2031, the second chute 221 slides along the second slide 2031 so that the lower clamping plate 22 slides along the surface of the lower fixing plate 203. A surface of the lower clamping plate 22 that is away from the lower fixing plate 203 is a lower placing surface of the flexible display device. Furthermore, the second chute 221 is disposed on the lower clamping plate 22 facing the surface of the lower fixing plate 203. The lower placing surface of the flexible display device is provided with a second fixing clip 220 configured to fix a lower portion of the flexible display device. The second fixing clip 220 disposed on two sides of the lower clamping plate 22, and the second fixing clip 220 can fix the lower portion of the flexible display device so that the flexible display device is fixed on the lower clamping plate 22. When the lower clamping plate 22 is slid relative to the surface of the lower fixing plate 203, the flexible display device is stopped relative to the lower clamping plate 22.

The first tension measuring element 23 is disposed on an end of the upper bending plate 202 that is away from the bending shaft 201, and connected to an end of the upper clamping plate 21 that is away from the bending shaft 201. The second tension measuring element 24 is disposed on an end of the lower fixing plate 203 that is away from the bending shaft 201, and connected to an end of the lower clamping plate 22 that is away from the bending shaft 201. The first tension measuring element 23 and the second tension measuring element 24 are tension sensors.

Figure 3:
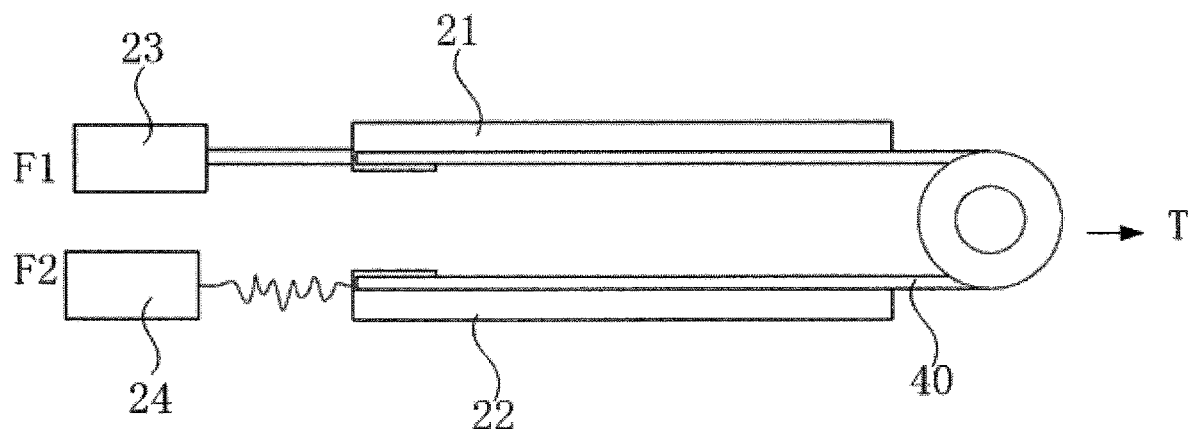
FIG. 3 is a force analysis chart of the bending test device for the flexible display device of the present disclosure.

Referring to FIG. 3, a force analysis chart of the bending test device for the flexible display device of the present disclosure is illustrated. When the upper bending plate 202 is rotated by driving the bending shaft 201, the upper clamping plate 21 is moved relative to the upper bending plate 202. A force F1 facing the bending shaft 201 is generated for the first tension measuring element 23, and the first tension measuring element 23 can measure the force F1. The lower clamping plate 22 is moved relative to the lower fixing plate 203. A force F2 facing the bending shaft 201 is generated for the second tension measuring element 24, and the second tension measuring element 24 can measure the force F2. The flexible display device 40 is disposed on the upper clamping plate 21 and the lower clamping plate 22. When the upper bending plate 202 is rotated by driving the bending shaft 201, the flexible display device 40 is bent, wherein a bending stress T generated at a bending portion is the sum of the force F1 and force F2 so that the bending stress of the bending portion of the flexible display device 40 can be measured. A rotation angle of the upper bending plate 202 is changed to differ the bending degree of the flexible display device 40. Thus, the bending degree of the flexible display device 40 can obtain to evaluate the bending ability of the flexible display device 40.

Preferably, if the bending ability of the flexible display device 40 is evaluated with some bending stress, we can disposed a flexible connection at least formed between the first tension measuring element 23 and the upper clamping plate 21, or formed between the second tension measuring element 24 and the lower clamping plate 22, such as, a spring connection is disposed, and changing the elasticity coefficient of the spring can quantitatively control the stress T. For example, a distance between the first tension measuring element 23 and the upper clamping plate 21 is kept, and the spring constant of the spring connected between the first tension measuring element 23 and the upper clamping plate 21 is changed so that the elasticity the spring connected between the first tension measuring element 23 and the upper clamping plate 21 can be quantified. A distance between the second tension measuring element 24 and the lower clamping plate 22 is kept, and the spring constant of the spring connected between the second tension measuring element 24 and the lower clamping plate 22 is changed so that the elasticity the spring connected between the second tension measuring element 24 and the lower clamping plate 22 can be quantified. Thus, we can evaluate the bending ability of the flexible display device with some bending stress.

Preferably, a shaft sleeve 2010 is disposed on the bending shaft 201, at least one bearing 2020 is disposed in the shaft sleeve 2010 so that the shaft sleeve 2010 and the flexible display device 40 have synchronized movement. The shaft sleeve 2010 and the flexible display device 40 do not generate friction to avoid damage to the flexible display device 40.

Figure 4:
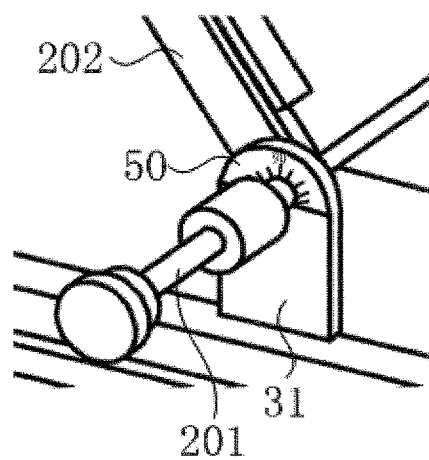
FIG. 4 is a partial view of the bending test device for the flexible display device of the present disclosure.

Preferably, the bending test device further comprises an angle plate 50, the angle plate 50 is disposed on a side of the bending shaft 201. In the specific embodiment, the angle plate 50 is fixed on the stand 31 or formed on the stand 31. The angle plate 50 does not rotate by driving of the bending shaft 201. The angle plate 50 is formed with an angular scale. Referring to FIG. 4, a partial view of the bending test device for the flexible display device of the present disclosure is illustrated. When the bending shaft 201 of the bending device 20 is bent an angle, the angle plate 50 can read the angle between the bending device 20 and a level. The advantage is that the data is intuitive, simple, and clear.

Figure 5:
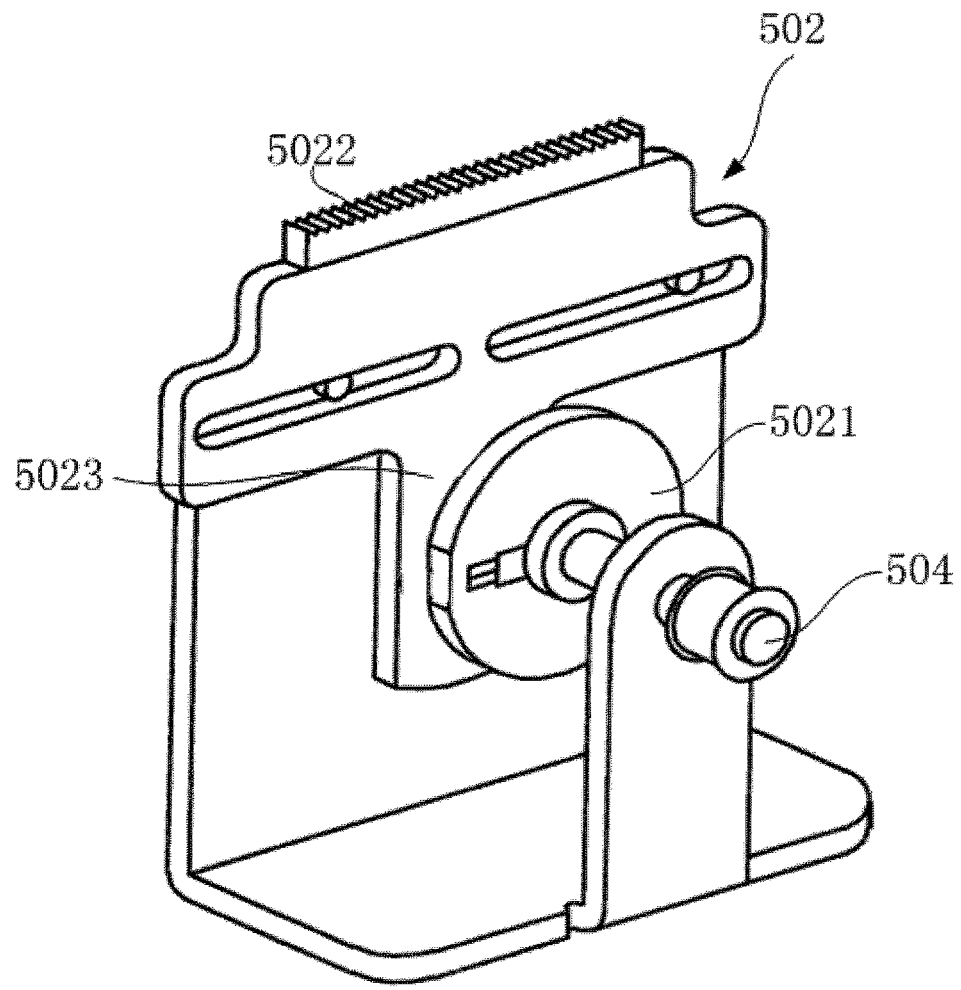
FIG. 5 is a schematic view of a motion device of the bending test device for the flexible display device of the present disclosure.
Figure 6:
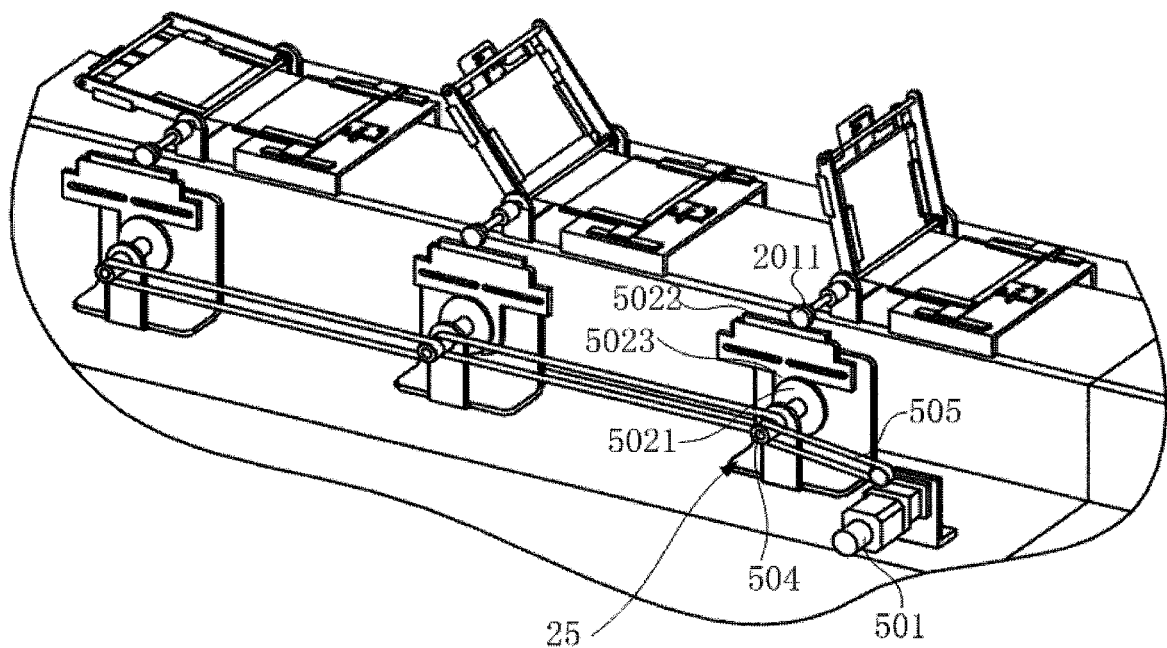
FIG. 6 is a schematic view of a bending test system for the flexible display device of the present disclosure.

FIG. 5 is a schematic view of a motion device of the bending test device for the flexible display device of the present disclosure, and FIG. 6 is a schematic view of a bending test system for the flexible display device of the present disclosure. Referring to FIGS. 2, 5, and 6, the bending test device for the flexible display device further comprises a motion device 25, wherein the motion device 25 is fixedly connected to the workbench 30. The motion device 25 is connected to at least one end of the bending shaft 201 to drive the bending shaft 201 rotated. The bending shaft 201 and a connecting end of the motion device are provided with a gear 2011.

The motion device 25 comprises a motor 501 and a crank slider mechanism 502. The motor 501 is connected to the crank slider mechanism 502 through a driving shaft 504. The motor 501 is connected to the driving shaft 504 through a transmission belt 505. The motor 501 drives the driving shaft 504 to rotate through the transmission belt 505. The crank slider mechanism 502 comprises a cam 5021 and a rack 5022, and the rack 5022 connects to an edge of the cam 5021 through a connecting rod 5023. The motor 501 is connected to the cam 5021 of the crank slider mechanism 502 through the driving shaft 504. The driving shaft 504 is rotated by driving the motor 501, and the driving shaft 504 drives the cam 5021 to rotate. The cam 5021 drives the rack 5022 using a reciprocating motion through the rod 5023 so that rotational motion of the motor is converted to rectilinear motion. Preferably, the diameter of the cam 5021 is greater than the diameter of the driving shaft 504. The high-speed rotation of the motor 501 can convert to the low-speed rotation of the cam 5021. Thus, a deceleration function can be implemented.

In the present disclosure, the crank slider mechanism 502 is configured to convert rotational motion of the motor 501 to rectilinear motion, and the rack 5022 is moved to a reciprocating motion. The rack 5022 has a gear, and is engaged with the gear of the bending shaft 201. The rectilinear motion of the rack 5022 is converted to a rotational motion of the gear 2011 so that the bending shaft 201 rotates. Preferably, adjusting a diameter of plate 5042 can control the reciprocating motion of the rack 5022 so that the rotation angle of the gear 2011 can be controlled.

The working process of the bending test device for the flexible display device is as follows.

The upper portion and the lower portion of the flexible display device 40 are fixed on the upper clamping plate 21 and the lower clamping plate 22, respectively. An end of the flexible display device 40 with a flexible circuit board can dispose on the lower clamping plate 22 of the lower fixing plate 203. It can avoid bending the flexible circuit board of the flexible display device 40 to affect the performance of the flexible display device 40. Turning on the motion device, the motion device drives the bending shaft 201 to rotate. The bending shaft 201 drives the upper bending plate 202 to move to the lower fixing plate 203 so that the flexible display device 40 is bent. The bending stress of the flexible display device 40 can be obtained through the first tension measuring element 23 and the second tension measuring element 24, and the bending stress can be quantitatively controlled.

The present disclosure further provides a bending test system for the flexible display device. Referring to FIG. 6, a schematic view of a bending test system for the flexible display device of the present disclosure is illustrated. A plurality of bending test devices are disposed on the workbench 30. Preferably, each of two adjacent bending test devices are driven through the transmission belt 505 disposed on the driving shaft 504, the motor 501 connects to one of the bending test devices so that all bending test devices are driven by the transmission belt.

The present disclosure has been described with preferred embodiments thereof and it is understood that many changes and modifications to the described embodiments can be carried out without departing from the scope and the spirit of the invention that is intended to be limited only by the appended claims.

What is claimed is:

1. A bending test device for a flexible display device, comprising:
   a bending device comprising a bending shaft, an upper bending plate, and a lower fixing plate, wherein the bending shaft is disposed between the upper bending plate and the lower fixing plate, an end of the upper bending plate is fixedly connected to the bending shaft, the bending shaft is configured to rotate to move the upper bending plate to rotate toward the lower fixing plate, and the lower fixing plate is fixed on a workbench;
   an upper clamping plate disposed on a surface of the upper bending plate, wherein the upper clamping plate is configured to slide along the surface of the upper bending plate, a surface of the upper clamping plate that is away from the upper bending plate is an upper placing surface for the flexible display device, and the upper placing surface for the flexible display device is provided with a first fixing clip configured to fix an upper portion of the flexible display device;
   a lower clamping plate disposed on a surface of the lower fixing plate, wherein the lower clamping plate is configured to slide along the surface of the lower fixing plate, a surface of the lower clamping plate that is away from the lower fixing plate is a lower placing surface for the flexible display device, and the lower placing surface for the flexible display device is provided with a second fixing clip configured to fix a lower portion of the flexible display device;
   a first tension measuring element disposed on an upper portion of the upper bending plate and connected to an end of the upper clamping plate that is away from the bending shaft;
   a second tension measuring element disposed on a lower portion of the lower fixing plate and connected to an end of the lower clamping plate that is away from the bending shaft, and a flexible connection is at least formed between the first tension measuring element and the upper clamping plate, or formed between the second tension measuring element and the lower clamping plate; and
   a motion device connected to at least one end of the bending shaft and configured to drive the bending shaft to rotate, wherein the bending shaft and a connecting end of the motion device are provided with a gear, the motion device comprises a motor and a crank slider mechanism, the crank slider mechanism comprises a cam and a rack, the motor is connected to the cam through a driving shaft, the rack is connected to an edge of the cam through a connecting rod, the crank slider mechanism is configured to convert rotational motion of the motor to rectilinear motion of the rack, the rack is engaged with the gear of the bending shaft, and the rectilinear motion of the rack is converted to rotational motion of the gear so that the bending shaft rotates;
   wherein a shaft sleeve is disposed on the bending shaft, at least one bearing is disposed in the shaft sleeve so that the shaft sleeve and the flexible display device have synchronized movement.

2. A bending test device for a flexible display device, comprising:
   a bending device comprising a bending shaft, an upper bending plate, and a lower fixing plate, wherein the bending shaft is disposed between the upper bending plate and the lower fixing plate, an end of the upper bending plate is fixedly connected to the bending shaft, the bending shaft is configured to rotate to move the upper bending plate to rotate toward the lower fixing plate, and the lower fixing plate is fixed on a workbench;
   an upper clamping plate disposed on a surface of the upper bending plate, wherein the upper clamping plate is configured to slide along the surface of the upper bending plate, a surface of the upper clamping plate that is away from the upper bending plate is an upper placing surface for the flexible display device, and the upper placing surface for the flexible display device is provided with a first fixing clip configured to fix an upper portion of the flexible display device;
   a lower clamping plate disposed on a surface of the lower fixing plate, wherein the lower clamping plate is configured to slide along the surface of the lower fixing plate, a surface of the lower clamping plate that is away from the lower fixing plate is a lower placing surface for the flexible display device, and the lower placing surface for the flexible display device is provided with a second fixing clip configured to fix a lower portion of the flexible display device;

a first tension measuring element disposed on an upper portion of the upper bending plate and connected to an end of the upper clamping plate that is away from the bending shaft; and a second tension measuring element disposed on a lower portion of the lower fixing plate and connected to an end of the lower clamping plate that is away from the bending shaft;

wherein a shaft sleeve is disposed on the bending shaft, at least one bearing is disposed in the shaft sleeve so that the shaft sleeve and the flexible display device have synchronized movement.

3. The bending test device for the flexible display device according to claim 2, wherein the bending test device further comprises an angle plate, the angle plate is disposed on the bending shaft and located at a side of the upper bending plate, the angle plate is formed with an angular scale.

4. The bending test device for the flexible display device according to claim 2, wherein a flexible connection is at least formed between the first tension measuring element and the upper clamping plate, or formed between the second tension measuring element and the lower clamping plate.

5. The bending test device for the flexible display device according to claim 2, wherein a surface of upper bending plate is disposed with a first slide, and the upper clamping plate is disposed with a first chute corresponding to the first slide, the first chute slides along the first slide so that the upper clamping plate slides along the surface of the upper bending plate; a surface of lower fixing plate is disposed with a second slide, and the lower clamping plate is disposed with a second chute corresponding to the second slide, the second chute slides along the second slide so that the lower clamping plate slides along the surface of the lower fixing plate.

6. The bending test device for the flexible display device according to claim 2, wherein the bending test device further comprises a motion device, the motion device is connected to at least one end of the bending shaft and configured to drive the bending shaft to rotate.

7. The bending test device for the flexible display device according to claim 6, wherein the bending shaft and a connecting end of the motion device are provided with a gear, the motion device comprises a motor and a crank slider mechanism, the crank slider mechanism comprises a cam and a rack, the motor is connected to the cam through a driving shaft, the rack connects to an edge of the cam through a connecting rod, the crank slider mechanism is configured to convert a rotational motion of the motor to a rectilinear motion of the rack, the rack is engaged with to the gear of the bending shaft, and the rectilinear motion of the rack is converted to a rotational motion of the gear so that the bending shaft rotates.

8. The bending test device for the flexible display device according to claim 7, wherein the motor is connected to the driving shaft through a transmission belt.

9. A bending test system for a flexible display device including a plurality of bending test devices according to claim 2.

10. The bending test system for the flexible display device according to claim 9, wherein each of two adjacent bending test devices are driven through a transmission belt disposed on a driving shaft, a motor connects to one of the bending test devices so that all bending test devices are driven by the transmission belt.

* * * * *

UNITED STATES PATENT AND TRADEMARK OFFICE
CERTIFICATE OF CORRECTION

| | | |
|---|---|---|
| PATENT NO. | : 10,557,781 B2 | Page 1 of 1 |
| APPLICATION NO. | : 15/735311 | |
| DATED | : February 11, 2020 | |
| INVENTOR(S) | : Wen Han, Rong Ma and Jichuan Liu | |

It is certified that error appears in the above-identified patent and that said Letters Patent is hereby corrected as shown below:

On the Title Page

In (73) Assignee, change "WUHAN CHINA STAR OPTOELECTRONICS SEMICONDUCTOR DISPLAY TECHNOLOY CO., LTD. (Wuhan, Hubei, CN)" to -- WUHAN CHINA STAR OPTOELECTRONICS SEMICONDUCTOR DISPLAY TECHNOLOGY CO., LTD. (Wuhan, Hubei, CN) --.

Signed and Sealed this
Fifth Day of May, 2020

Andrei Iancu
*Director of the United States Patent and Trademark Office*